United States Patent [19]

Synek

[11] Patent Number: 5,612,048
[45] Date of Patent: Mar. 18, 1997

[54] STABILIZED MOISTURE-SENSITIVE PESTICIDE COMPOSITION AND METHOD OF MAKING

[75] Inventor: Joseph Synek, Overland Park, Kans.

[73] Assignee: AMVAC Chemical Corporation, Los Angeles, Calif.

[21] Appl. No.: 343,705

[22] Filed: Nov. 22, 1994

[51] Int. Cl.$^6$ .................................................. A61K 31/545
[52] U.S. Cl. ............................................ 424/409; 424/405
[58] Field of Search .................. 424/409; 514/772.6, 514/951, 952; 524/556; 252/351, 354, 356

[56] References Cited

U.S. PATENT DOCUMENTS

| | | | |
|---|---|---|---|
| 4,634,697 | 1/1987 | Hamashima | 514/202 |
| 4,867,972 | 9/1989 | Girardeau et al. | 424/409 |

OTHER PUBLICATIONS

Aries, *Chemical Abstracts*, vol. 81, 1975, #4 6396.
Barbulescu et al., *Chemical Abstracts*, vol. 108, 1982, #182, 241.
Bencsits, *Chemical Abstracts*, vol. 119, 1992, #175, 913.
Henderson et al., *Biological Abstracts*, vol. 94, 1993, #19309.

Primary Examiner—Thurman K. Page
Assistant Examiner—Sharon Howard
Attorney, Agent, or Firm—Loeb & Loeb LLP

[57] ABSTRACT

A stabilized moisture-sensitive pesticide composition comprises (a) a moisture-sensitive pesticide and (b) a moisture barrier component selected from the group consisting of a fatty acid, an alkyl ester of a fatty acid and combinations thereof in an amount effective to reduce the degradation of the pesticide due to exposure to moisture.

24 Claims, No Drawings

STABILIZED MOISTURE-SENSITIVE PESTICIDE COMPOSITION AND METHOD OF MAKING

FIELD OF THE INVENTION

The present invention relates to improved pesticide formulations and methods for producing them. More specifically, the present invention relates to stabilized moisture-sensitive pesticides having improved shelf life due to increased moisture resistance.

BACKGROUND OF THE INVENTION

Dry powdered pesticide compositions are known which include a diluent, wetting and dispersing agents, penetrating agents, foam stabilizers, couplers, and a variety of other materials to enhance the stability of the pesticide and improve the salability of the composition. A number of pesticides, however, are unstable in the dry powdered form due to sensitivity to moisture.

Attempts to solve the instability of such pesticides to moisture have centered on provision of a water scavenger or moisture barrier compound or combination thereof. In years past, the selection of a suitable water scavenger or mixture of scavengers was made readily by one skilled in the art in accordance with known principles and properties as set forth in various journals and publications by the suppliers of such materials, and in reference works such as McCutcheon's Handbook, Volume 1: Emulsifiers and Detergents (1991 North American Ed., McCutcheon Division, MC Publishing Co.) and in McCutcheon's Handbook, Volume 2: Functional Materials (1992 North American Ed., McCutcheon Division, MC Publishing Co.).

Epichlorohydrin was the best known scavenger available for many years. This compound was found to be acceptable by EPA for use in pesticide formulations and was permitted for use on growing crops. It has recently been ruled, however, that epichlorohydrin can no longer be used for formulae applied directly to growing crops.

Chemists have been searching for scavengers that are useful in bonding the free moisture in dry pesticide formulations and thus preventing the moisture from coming into contact with the pesticide. Such scavengers are desired to minimize decomposition of the pesticide and extend the shelf life of the product so that the product becomes commercially feasible. A number of different approaches to solving the problem of rapid degradation of the pesticide by small amounts of moisture have been attempted.

It has been proposed to use various types of surfactants. Nonionic surfactants such as those developed and marketed in the industry as alkylphenoxy polyethoxy ethanols, or those generally described as octyl or nonylphenol hydrophobes, have been suggested. Examples of such materials include adducts of 8 to 10 moles of ethylene oxide with octyl or nonyl phenol.

Use of anionic surfactants has also been considered. One exemplary anionic surfactant is sodium lauryl sulfate, which is also useful as a wetting agent which is required to wet the powder in the spray water as well as wet the leaf surfaces to which the pesticide composition is to be applied. It was believed that this type of chemistry would be helpful in bonding the free moisture in the formulae.

However, none of the known surfactants have proven useful as moisture barriers or scavengers for dry pesticide compositions.

Solvents such as alcohols, propylene glycol, ethylene glycol butyl ether, butyrolactone and tetrahydrofurfuryl alcohol have been possible candidates as moisture scavengers since they also have the ability to hold and bond water. However, the flammability of these solvents would make powdered products dangerous to manufacture and store.

It would be desirable to provide a dry pesticide composition which is stabilized against degradation due to contact with moisture. The composition desirably would include a stabilizer which is environmentally friendly, safe to use and store, and compatible with the pesticides with which it is combined in the dry composition.

SUMMARY OF THE PREFERRED EMBODIMENTS

In accordance with one aspect of the present invention, there has been provided a stabilized moisture-sensitive pesticide composition which comprises a moisture-sensitive pesticide and a moisture barrier component, more particularly a fatty acid, an alkyl ester of a fatty acid or a combination thereof. The moisture barrier component is present in an amount effective to reduce the degradation of the pesticide due to exposure to moisture.

In a more specific embodiment, the moisture barrier component is a $C_{1-4}$ alkyl ester, particularly a methyl ester, of a fatty acid or a combination of such esters.

In accordance with another aspect of the present invention, there is provided a method of producing a stabilized moisture-sensitive pesticide composition which comprises the step of combining a moisture-sensitive pesticide with an amount of a moisture barrier component as described herein which is effective to reduce the degradation of said pesticide due to exposure to moisture.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

It has been unexpectedly discovered that a fatty acid or combination of fatty acids, or an alkyl ester or a combination of such esters, acts as a moisture barrier and effectively stabilizes a dry pesticide composition against damage due to exposure to water. The moisture barrier inhibits contact between water and the water-sensitive pesticide, and also acts as a barrier between the pesticide and free acids, alkali and trace metals such as iron, magnesium, etc. which may be present on diluents employed in the composition. Such protection results in extended shelf life for the pesticide composition.

As used herein, the term "degradation" denotes loss of the active ingredient, i.e., the water-sensitive pesticide, as a result of contact with water, and also includes loss of the active ingredient due to contact with free acids, alkali and trace metals. Degradation can be determined simply by measuring the amount of the active ingredient present before and after contact with water.

The moisture barrier component is employed according to the invention in a dry pesticide composition in an amount effective to reduce the degradation of the pesticide due to exposure to moisture.

Fatty acids which are suitably esterified for use in the invention include, without limitation, caprylic acid, capric acid, lauric acid, myristic acid, palmitic acid, stearic acid and oleic acid.

In addition, many vegetable oils can serve as sources of fatty acids for esterification to produce compounds useful according to the invention. Vegetable oils include a variety of different fatty acids. Useful vegetable oils include, without limitation, cottonseed oil, peanut oil, coconut oil, corn oil, rape seed oil, safflower oil, olive oil and the like.

Preferred esters for use according to the invention include methyl, ethyl, propyl and butyl esters of the foregoing fatty acids. Methyl esters are particularly preferred.

One of the criteria of determining which material can be used is its physical miscibility with the pesticide which it is to protect. If the material is not miscible with the specific pesticide, the moisture barrier formed may be less effective then one in which the pesticide is miscible. For example, methylation of fatty acids typically affords a compound which is compatible with the pesticide, whereas the pesticide may not be compatible with non-esterified fatty acids or vegetable oils. By the same token, however, non-esterified fatty acids and vegetable oils which are miscible with the pesticide to be protected can be employed according to the instant invention as moisture barriers, and all such materials are contemplated for use according to the instant invention.

Typically the moisture barrier component is employed according to the invention in an amount from about 5 to 15 wt %, more particularly 7 to 12 wt %, based on the entire weight of the pesticide composition. The range in amounts of the moisture barrier component may be more or less depending on factors such as the pesticide concentration, the presence of trace minerals, the sensitivity of the pesticide to moisture and the acidity or alkalinity of the overall composition.

A variety of moisture-sensitive pesticides are advantageously provided as dry compositions according to the present invention. Moisture-sensitive organic phosphate pesticides that are completely or partially water miscible, such as Mevinphos, Dicrotophos, Oxydemeton-methyl, Metam sodium, Dichlorvos, Trichlorfon and Monocrotophos, are particularly suitable for protection according to the invention, and are afforded increased shelf life longevity. It is contemplated that any pesticide which is sensitive to moisture, acids, alkalis or free metals can be protected according to the present invention, and all such pesticides are considered to be useful in compositions of the present invention.

One or more conventional additives may be combined with the selected moisture barrier component and pesticide to produce a composition according to the invention. Such additives include, without limitation, diluents, wetting agents, dispersing agents, antifoam agents, stickers, colorants, perfumes, chelating agents and the like.

In a preferred embodiment, a diluent is impregnated with the selected moisture barrier component. Suitable diluents include silicas of various types, diatomaceous earth, attapulgites, montmorillonites, kaolins, talcs and mixtures thereof. Silicas are preferred since they absorb a higher concentration of liquid, thus allowing a greater concentration of pesticide in the composition.

A typical composition according to the invention includes the following formulation:

| | |
|---|---|
| Methylated ester of fatty acids | 12 parts |
| Pesticide | 45 parts |
| Diluent (Carrier) | 40 parts |
| Wetting/Dispensing Agent | 3 parts |
| Total: | 100 parts |

Compositions having other formulations within the scope of the invention can readily be prepared by those skilled in the art.

The compositions of the invention typically have a shelf life of at least two or more years, based on accelerated storage data conducted at 40° C. (105° F.) as compared to most products that are moisture sensitive.

The use of moisture barrier components, such as esters of fatty acids or vegetable oils, according to the invention enables preparation of pesticides, which otherwise would be in highly toxic and hard-to-handle liquid form, to be prepared as powdered compositions. Such compositions are much easier and safer to handle for agricultural, industrial and specialty uses. The safety in handling alone will protect the applicator from possible injury where previously the applicator had to use highly flammable formulae of the same pesticides containing such solvents as acetone, methyl isobutyl ketone, isopropyl alcohol, methyl alcohol, cyclohexanone and the like. The inventive pesticide compositions obviate the need for placing such solvents into the environment and exposing the worker applicator or aerial applicator to consequent hazardous conditions.

Furthermore, the moisture barrier components employed according to the invention are biodegradable. Similarly, pesticide compositions according to the invention can be conveniently prepared in packages, comprised for example of water-soluble PVA (polyvinyl acetate). Such packages can be disposed of within the environmental guidelines set for the standard landfill, rather than requiring disposal in an EPA approved hazardous waste area. Disposal cost reductions can thus be realized to the user, as well as to the city, state or federal government.

The invention is further illustrated by the following non-limiting examples. All parts are by weight unless otherwise expressed.

Pesticide compositions 1–6, which were not stabilized in accordance with the present invention, were tested and showed rapid degradation. The samples included a reduction in the amount of the active ingredient (25% active ingredient) to determine if dilution of the active ingredient would stabilize the formulae.

| Example 1 | |
|---|---|
| Mevinphos Technical | 25 parts |
| Tetrahydrofurfuryl alcohol | 5 parts |
| Silica Precipated Amphorous (Zeolex 7A) | 70 parts |
| Total: | 100 parts |
| Example 2 | |
| Mevinphos Technical | 25 parts |
| Cab-O-Sil L 90 | 5 parts |
| Silica Precipated Amphorous (Zeolex 7A) | 70 parts |
| Total: | 100 parts |

Example 3

| | |
|---|---|
| Mevinphos Technical | 25 parts |
| Calcium Carbonate | 3 parts |
| Silica Precipated Amphorous (Zeolex 7A) | 72 parts |
| Total: | 100 parts |

Example 4

| | |
|---|---|
| Mevinphos Technical | 25 parts |
| Water | 5 parts |
| Silica Precipated Amphorous (Zeolex 7) | 70 parts |
| Total: | 100 parts |

Example 5

| | |
|---|---|
| Mevinphos Technical | 25 parts |
| Diatomaceous Earth | 75 parts |
| Total: | 100 parts |

Example 6

| | |
|---|---|
| Mevinphos Technical | 25 parts |
| Diatomaceous Earth with lower alkalinity | 75 parts |
| Total: | 100 parts |

The water content of the diluents can vary depending upon the current humidity at time of packaging and their exposure during storage.

Alkalinity and Acidity of the carriers:

| | |
|---|---|
| Zeolex 7A | ph value range: 6–7 |
| Diatomaceous earth | ph value range: 9–10 |
| Lower alkaline DE | ph value range: 8–9 |

The comparative compositions showed storage losses as indicated in Table I below.

TABLE I

Storage @ 1 month at 40° C.

| Example | Percentage Loss |
|---|---|
| 1 | 29% |
| 2 | 23% |
| 3 | 41% |
| 4 | 36% |
| 5 | 30% |
| 6 | 26% |

The compositions greater water content as well as the one with relatively high alkalinity showed more rapid decomposition. The observed rate of loss is too great to sell the product commercially.

Compositions 7–10 were produced in accordance with the present invention. These compositions include different components but with show similar chemistries.

Example 7

| | |
|---|---|
| Mevinphos Technical | 50 parts |
| Silica Precipated Amphorous | 50 parts |
| Total: | 100 parts |

Example 8

| | |
|---|---|
| Mevinphos Technical | 50 parts |
| Methyl Oleate | 7 parts |
| Polyoxyethylene sorbitan stearate | 3 parts |
| Silica Precipated Amphorous | 40 parts |
| Total: | 100 parts |

Example 9

| | |
|---|---|
| Mevinphos Technical | 35 parts |
| Methyl Oleate | 12 parts |
| Polyoxyethylene sorbitan laurate | 3 parts |
| Silica Precipated Amphorous | 50 parts |
| Total: | 100 parts |

Example 10

| | |
|---|---|
| Dicrotophos Technical | 40 parts |
| Methyl Caprylate-Caprate | 12 parts |
| Polyoxyethylene sorbitan laurate | 3 parts |
| Silicon Precipated Amphorous | 50 parts |
| Total: | 100 parts |

A comparison of the stability of Examples 7 through 10 is shown in Tables II–V below.

TABLE II

Example 7
Storage Time In Months

| Storage Temperature | 1 month | 2 months |
|---|---|---|
| 40° C. | 45.9% | 41.1% |
| 0° C. | 51.0% | 51.3% |

TABLE III

Example 8

| Storage Temperature | 1 month | 2 months | 3 months | 4 months |
|---|---|---|---|---|
| 40° C. | 51.5% | 47.5% | 46.2% | 43.8% |
| 0° C. | — | — | 53.1% | 52.3% |

TABLE IV

Example 9

| Storage Temperature | 1 month | 2 months |
|---|---|---|
| 40° C. | — | 33.9% |
| 0° C. | — | 34.2% |

TABLE V

Example 10

| Storage Temperature | 1 month | 3 months |
|---|---|---|
| 40° C. | 36.9% | 34.4% |
| 0° C. | 38.2% | 37.6% |

TABLE VI

Comparison of percent loss of active ingredient (Mevinphos) between samples 7, 8 and 9 at 2 month storage at 40° C.

| Example | % loss of active ingredient |
| --- | --- |
| 7 | 19.1 |
| 8 | 9.2 |
| 9 | 0.9 |

TABLE VII

Comparison of percent loss of active ingredient between samples 7 and 10 at one month storage at 40° C.

| Example | % loss of active ingredient |
| --- | --- |
| 7 | 10.0 |
| 10 | 0.96 |

The foregoing exemples demonstrate that dry pesticide compositions can be stabilized in accordance with the present invention against decomposition due to moisture.

What is claimed is:

1. A stabilized moisture-sensitive pesticide composition which comprises:
   (a) at least 25 wt % of a moisture-sensitive pesticide; and
   (b) from about 5 to 15 wt % of a moisture barrier component selected from the group consisting of a fatty acid, an alkyl ester of a fatty acid and a combination thereof wherein said moisture barrier component is effective to reduce the degradation of said moisture-sensitive pesticide due to exposure to moisture,
   wherein said stabilized moisture-sensitive pesticide composition has a dry powdered form.

2. The composition of claim 1 wherein said fatty acid is selected from the group consisting of caprylic acid, capric acid, lauric acid, myristic acid, palmitic acid, stearic acid and oleic acid.

3. The composition of claim 1 wherein said alkyl ester is a $C_{1-4}$ alkyl ester.

4. The composition of claim 3 wherein said ester is a methyl, ethyl, n-propyl or n-butyl ester.

5. The composition of claim 4 wherein said ester is a methyl ester.

6. The composition of claim 1 wherein said moisture barrier component is a vegetable oil or an esterification product of a vegetable oil.

7. The composition of claim 6 wherein said vegetable oil is selected from the group consisting of cottonseed oil, peanut oil, coconut oil, corn oil, rape seed oil, olive oil and safflower oil.

8. The composition of claim 1 wherein said moisture barrier component is present in an amount from about 7 to 12 wt %.

9. The composition of claim 1, wherein said moisture-sensitive pesticide is selected from the group consisting of mevinphos, dicrotophos, oxydemetonmethyl, metam sodium, dichlorvos, trichlorfon and monocrotophos.

10. The composition of claim 1, wherein said stabilized moisture-sensitive pesticide composition further comprises a diluent.

11. The composition of claim 10 wherein said diluent is selected from the group consisting of silicas, diatomaceous earth, attapulgites, montmorillonites, kaolins, talcs and mixtures thereof.

12. The composition of claim 11 wherein said diluent is impregnated with said ester or combination of esters.

13. A method of producing a stabilized moisture-sensitive pesticide composition which comprises the step of:
   combining a moisture-sensitive pesticide with an amount of a moisture barrier component selected from the group consisting of a fatty acid, an alkyl ester of a fatty acid and a combination thereof which is effective to reduce the degradation of said moisture-sensitive pesticide due to exposure to moisture,
   wherein said moisture-sensitive pesticide is employed in an amount of at least 25 wt % of said stabilized moisture-sensitive pesticide composition, said moisture barrier component is employed in an amount of from about 5 to 15 wt %, and said stabilized moisture-sensitive pesticide composition has a dry powdered form.

14. The method of claim 13 wherein said fatty acid is selected from the group consisting of caprylic acid, capric acid, lauric acid, myristic acid, palmitic acid, stearic acid and oleic acid.

15. The method of claim 13 wherein said alkyl ester is a $C_{1-4}$ alkyl ester.

16. The method of claim 15 wherein said ester is a methyl, ethyl, n-propyl or n-butyl ester.

17. The method of claim 16 wherein said ester is a methyl ester.

18. The method of claim 13 wherein said moisture barrier component is a vegetable oil or an esterification product of a vegetable oil.

19. The method of claim 18 wherein said vegetable oil is selected from the group consisting of cottonseed oil, peanut oil, coconut oil, corn oil, rape seed oil, olive oil and safflower oil.

20. The method of claim 13 wherein said moisture barrier component is employed in an amount from about 7 to 12 wt %.

21. The method of claim 13, wherein said moisture-sensitive pesticide is selected form the group consisting of mevinphos, dicrotophos, oxydemetonmethyl, metam sodium, dichlorvos, trichlorfon and monocrotophos.

22. The method of claim 13, wherein said stabilized moisture-sensitive pesticide composition further comprises a diluent.

23. The method of claim 22 wherein said diluent is selected from the group consisting of silicas, diatomaceous earth, attapulgites, montmorillonites, kaolins, talcs and mixtures thereof.

24. The method of claim 23 wherein said diluent is impregnated with said ester or combination of esters.

\* \* \* \* \*